US00PP33449P2

(12) United States Plant Patent
Martinez

(10) Patent No.: US PP33,449 P2
(45) Date of Patent: Sep. 7, 2021

(54) SEEDLESS TABLE GRAPE PLANT NAMED 'ITUMSIXTEEN'

(50) Latin Name: *Vitis vinifera*
Varietal Denomination: Itumsixteen

(71) Applicant: Investigacion y Tecnologia de Uva de Mesa S.L., Blanca (ES)

(72) Inventor: Manuel Tornel Martinez, La Alberca (ES)

(73) Assignee: Investigacion y Tecnologia de Uva de Mesa S.L.

( * ) Notice: Subject to any disclaimer, the term of this patent is extended or adjusted under 35 U.S.C. 154(b) by 0 days.

(21) Appl. No.: 17/015,487

(22) Filed: Sep. 9, 2020

(51) Int. Cl.
*A01H 5/08* (2018.01)
*A01H 6/88* (2018.01)

(52) U.S. Cl.
USPC ..... Plt./207
CPC ..... *A01H 6/88* (2018.05)

(58) Field of Classification Search
USPC ..... Plt./207
CPC ..... A01H 6/88; A01H 5/08
See application file for complete search history.

*Primary Examiner* — Keith O. Robinson
(74) *Attorney, Agent, or Firm* — Cassandra Bright

(57) ABSTRACT

A new and distinct variety of grapevine named 'Itumsixteen' is herein disclosed. 'Itumsixteen' abundantly forms medium sized light green to yellow colored berries with an attractive obovoid berry shape, a neutral aromatic flavor and a very crunchy and firm berry texture. Being mid-season variety, the fruit commonly is ready for harvesting in from July to early September in Blanca, Murcia, Spain. 'Itumsixteen' displays good eating qualities as a table grape, the fruit meatiness and firmness render the fruit amenable for handling, shipping, and storage.

5 Drawing Sheets

Latin name of the genus and species: *Vitis vinifera*.
Variety denomination: 'Itumsixteen'.

BACKGROUND OF THE INVENTION

A breeding program was initiated during 2003 at a research nursery in Blanca, Murcia, Spain. During the development of this breeding program, a new variety of *Vitis vinifera* was created by deliberate cross breeding of two parent plants by emasculation of the pollen bearing organ of the female and introducing pollen from another male origin. The female parent of the new variety is 'ITUM189-12', an unpatented proprietary selection. The male parent (i.e. the pollen parent) of the new variety is 'Princess', unpatented.

'Itumsixteen' was identified as a potentially interesting selection during 2007 at the same location in Murcia, Spain. After identifying the new variety as a potentially interesting selection, first propagation of 'Itumsixteen' by vegetative cuttings was undertaken during 2008, at the research nursery in Murcia, Spain. Controlled testing and propagation of the new variety continued, to assess stability of the unique characteristics of this variety. Subsequently, several generations have been reproduced and have shown that the unique features of this cultivar are stable and reproduced true to type. No publications have been issued on the plant breeding invention. No commercial sales occurred before the filing of the U.S. plant patent application.

SUMMARY OF THE INVENTION

The cultivar 'Itumsixteen' has not been observed under all possible environmental conditions. The phenotype may vary somewhat with variations in environment such as temperature, day length, and light intensity, without, however, any variance in genotype. The new variety 'Itumsixteen' is yellow to light green seedless table grape with medium production and a moderate fertility index "1, 3". In addition to the before mentioned characteristics, the following traits have been repeatedly observed and are determined to be the unique characteristics of 'Itumsixteen'. These characteristics in combination distinguish 'Itumsixteen' as a new and distinct *Vitis* cultivar:

1. Medium sized individual fruit with yellow to light green skin coloration; formed in medium-to-large clusters.
2. An attractive obovoid berry shape.
3. A mid-season season variety, commonly bears fruit for harvesting from July until early September in the region of Murcia, Spain.
4. Very firm berry texture.
5. Rudimentary seeds.
6. Resistance to cracking.
7. Fruit has been found to be suitable for handling and shipping.
8. Observed tolerance of water shortage.
9. Observed tolerance for temperatures up to 41° C.
10. Neutral aromatic flavor profile.

COMPARISON TO PARENT VARIETIES

TABLE 1

| Characteristic | 'Itumsixteen' | Parental A (fem) 'ITUM189-12' |
|---|---|---|
| Berry Shape | Obovoid | Cylindrical |
| Formation of Seeds | Rudimentary | Lignified |

TABLE 1-continued

| Characteristic | 'Itumsixteen' | Parental B (masc.) 'Princess' |
|---|---|---|
| Berry Flavor: | Neutral aromatic | Muscat |
| Berry Shape: | Obovoid | Cylindrical |

COMMERCIAL COMPARISON

TABLE 2

| Characteristic | 'Itumsixteen' | 'Moscatel de Alejandria' (unpatented) |
|---|---|---|
| Berry Flavor | Neutral aromatic | Muscat |
| Berry Shape | Obovoid | Ellipsoid |
| Presence of Seeds | Rudimentary | Complete |

| Characteristic | 'Itumsixteen' | 'Centennial Seedless' (unpatented) |
|---|---|---|
| Berry Shape | Obovoid | Cylindrical |
| Berry Flavor | Neutral aromatic | Muscat |

| Characteristic | 'Itumsixteen' | 'Autumn Seedless' (unpatented) |
|---|---|---|
| Berry Shape | Obovoid | Cylindrical |

BRIEF DESCRIPTION OF THE PHOTOGRAPHS

The accompanying photographic illustrations show typical samples of vegetative growth of a 5 year old specimen of the new variety, in color as nearly true as it is reasonably possible to make in a color illustration of this character. Plants were grown in Murcia, Spain. Colors in the photograph may differ from the color values cited in the detailed botanical description below, which accurately describes the colors of the new Grapevine.

DETAILED BOTANICAL DESCRIPTION

Figure 1:
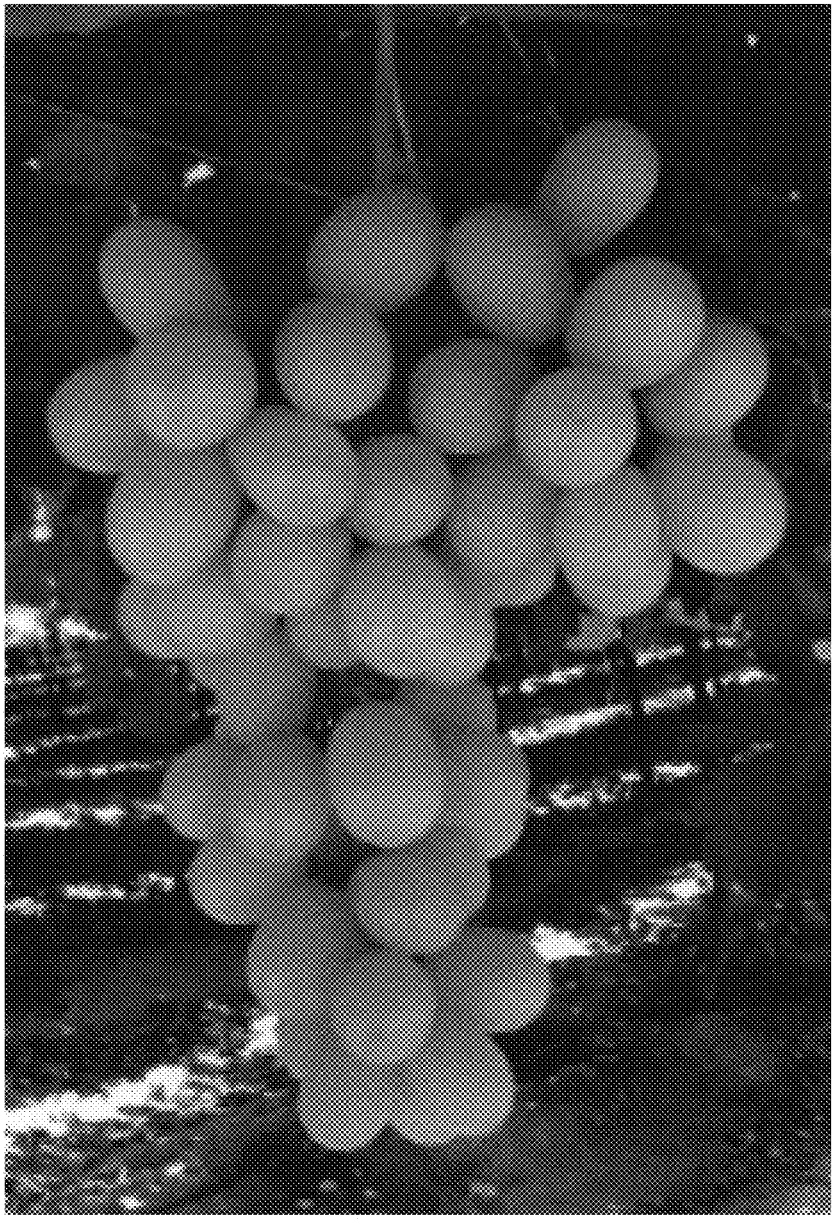
FIG. 1 illustrates a fruit cluster of 'Itumsixteen'.
Figure 2:
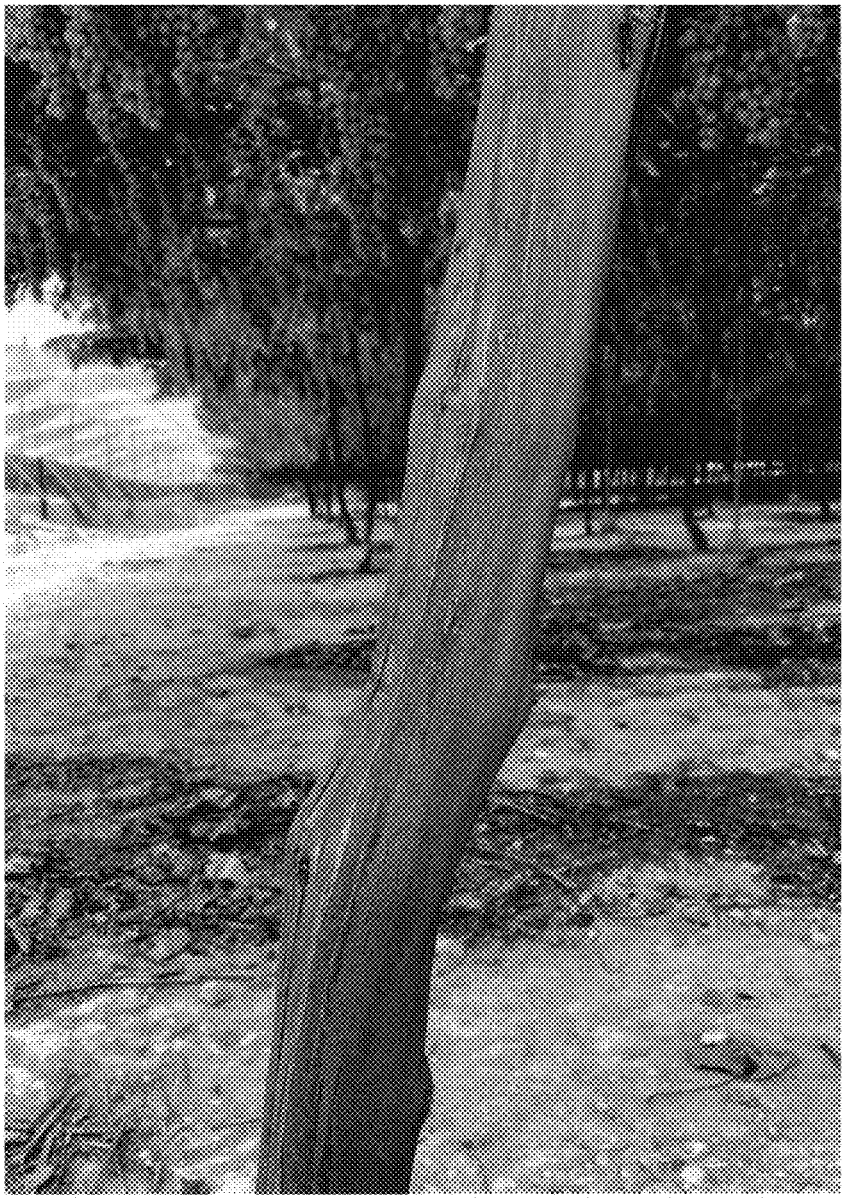
FIG. 2 shows a close-up view of the trunk of 'Itumsixteen'.
Figure 3:
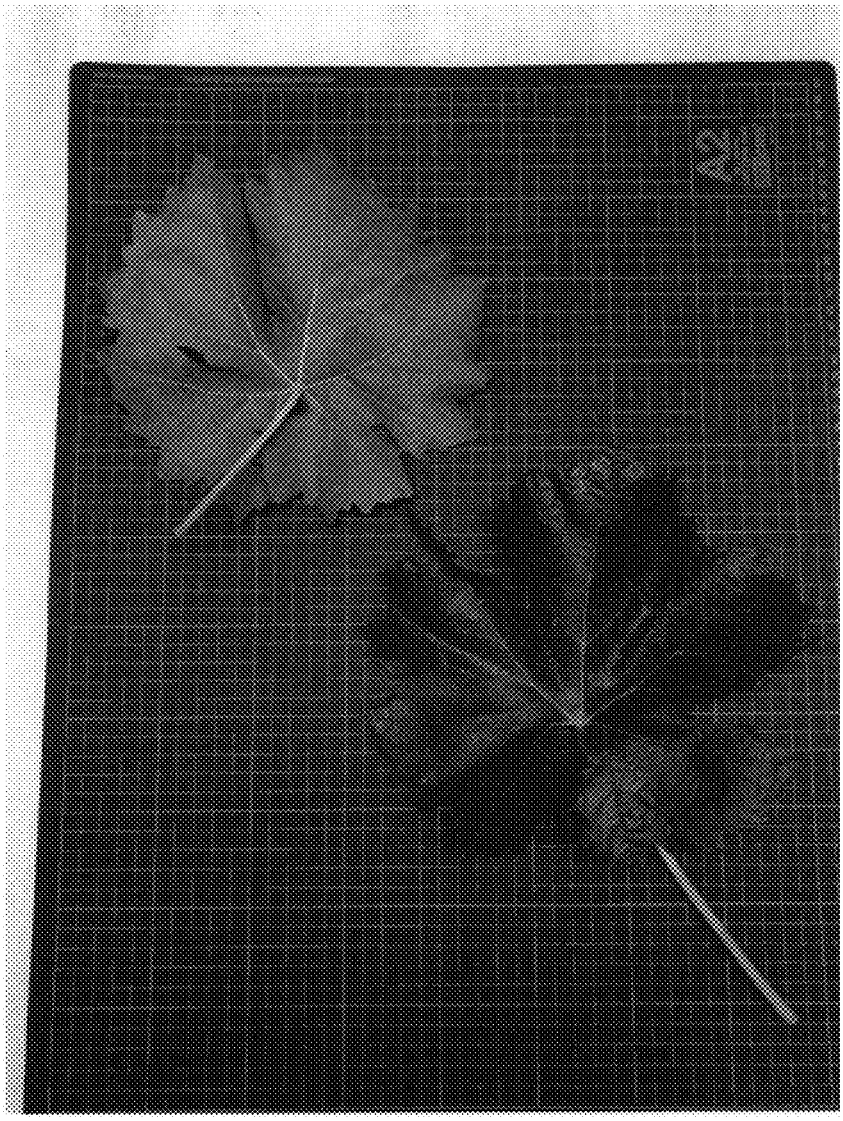
FIG. 3 illustrates in close up perspective typical foliage of the new variety, both front and back of the leaf.
Figure 4:
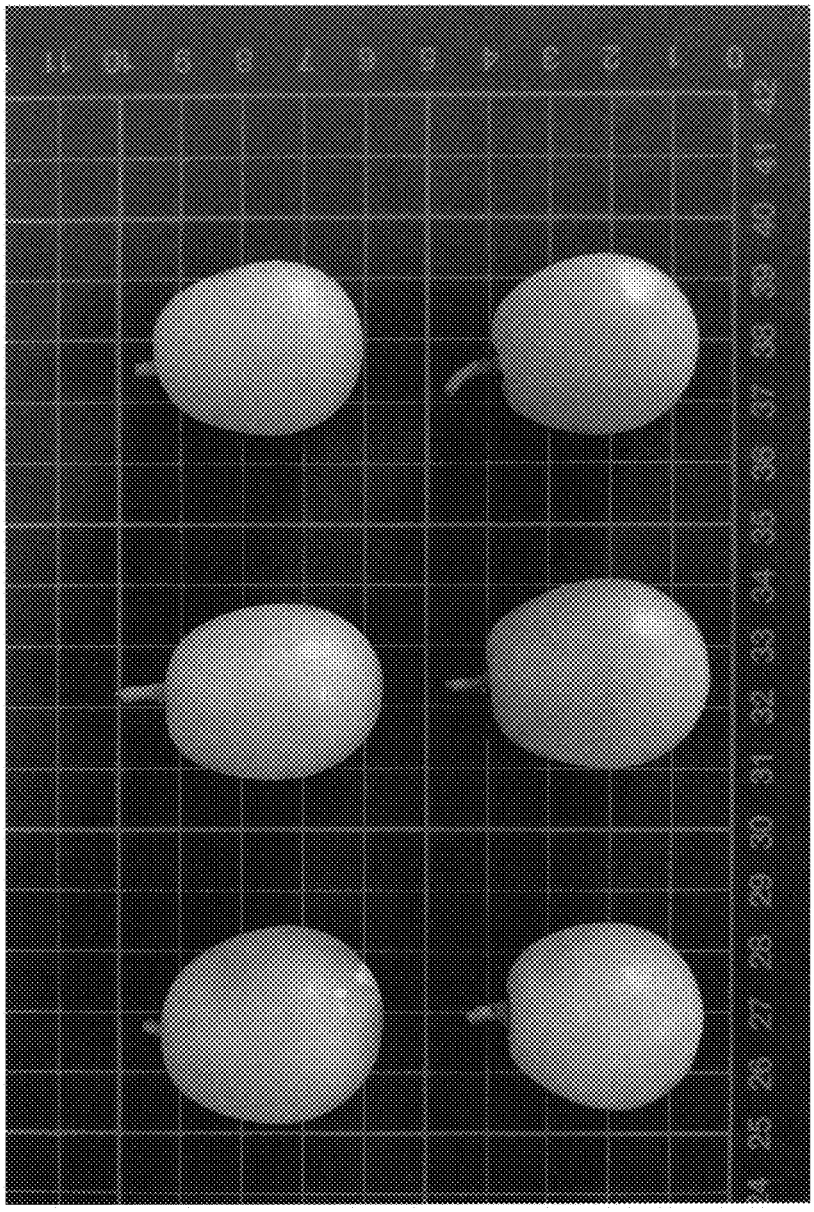
FIG. 4 illustrates individual berries of the new variety.
Figure 5:
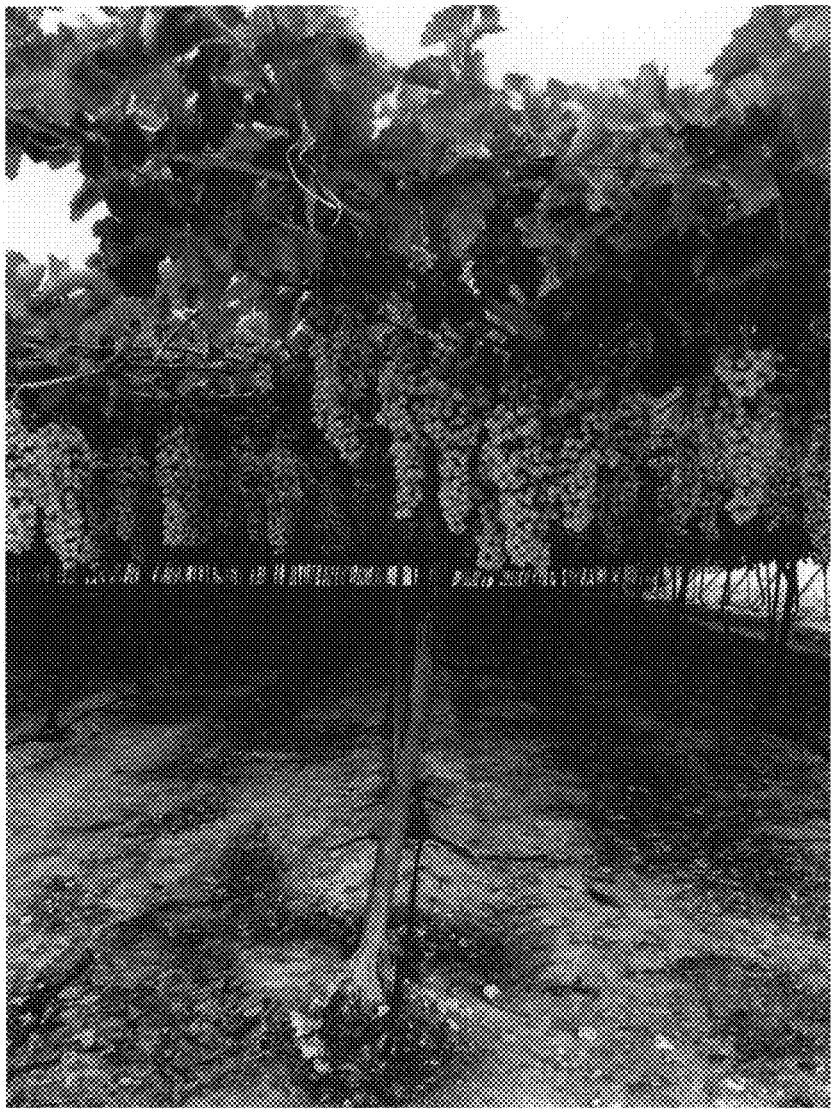
FIG. 5 illustrates a small test field of fruiting vines of the new variety.

In the following description, color references are made to The Royal Horticultural Society Colour Chart 2015 except where general terms of ordinary dictionary significance are used. Some descriptors, when useful have been incorporated from *UPOV Grape Descriptor Guidelines*. The description is based on the observation of plants growing on '1103 Paulsen' (unpatented) rootstock in clay stony soil conditions in the fields near Blanca, Murcia, Spain. The age of plant described is of 5 years, with an average height of 200 cm, a high canopy density, a 300 cm plant spread, a one-year growth rate to reach two meters high and 20 to 30 days to initiate roots at approx. 20° C. At observation location temperature ranged between 15° C. to 35° C. during the day, and between 5° C. to 20° C. during the night.

Botanical classification: *Vitis vinifera* 'Itumsixteen'.

CANES

Characteristics of mature canes:

*Diameter.*—1.6 to 2.4 cm.
*Length.*—60 to 80 cm.
*Color.*—Medium light brown (164C RHS).
*Cross section shape.*—Circle.
*Strength.*—Medium.
*Texture.*—Non-pubescent, rough.

Lenticels: Diameter.—<0.5 mm.
*Density.*—Few to-moderate.
*Color.*—Medium light brown (164C RHS).

Internode length: 14-16 cm; midpoint 16 cm.
*Pigmentation at internode, dorsal.*—Near RHS Greyed-Orange 164C.
*Pigmentation at internode, ventral.*—Near RHS Greyed-Orange 164C.

Tendril pattern on show: 0,0,0,0,0,1,0 or 0,0,0,0,0,0,1.
*Tendrils forked.*—Yes.
*Tendril texture.*—Glabrous.
*Tendril length.*—6 to 11 cm.

Bud width: 0.7 to 0.8 cm.
*Bud length.*—0.4 cm.
*Bud shape.*—Triangular.
*Bud color.*—Light yellow brown Near RHS Greyed-Yellow 161D, flushed 162D.

Young shoot:
*Openness of tip.*—Open.
*Tip pubescence.*—Absent to sparse.
*Anthocyanin not present in shoot pigmentation.*
*Texture.*—Smooth.
*Diameter.*—0.6 to 0.8 cm.
*Longitudinal length.*—1.6 to 3.0 m; average 1.8 m.
*Color.*—Near RHS Greyed-Orange 164D, streaked 165D.
*Cross section.*—Circular.
*Strength.*—Medium.
*Attitude.*—Semi-erect.
*Bark texture.*—Shaggy.
*Bark color.*—Near RHS Greyed-Red 178A streaked 180A.

FOLIAGE

Bud burst date: Mid March.

Leaf:
*Arrangement.*—Alternate.
*Quantity.*—Approximately 12 per cane.
*Average length.*—26 cm.
*Average width.*—21.5 cm.
*Overall shape of blade.*—Obovate.
*Apex.*—Acute.
*Base.*—Rounded.
*Margin.*—Shallow dentations. Dentations 5 to 8 mm in length, broadly deltate.
*Texture of top surface.*—Smooth.
*Texture of bottom surface.*—Smooth.
*Pubescence.*—None.
*Aspect.*—Undulate.
*Lobe quantity.*—Typically 3.

Sinuses:
*Shape of petiolar sinus.*—High widened, overlapped.
*Shape of base petiolar sinus.*—High widened, overlapped.
*Depth of petiolar sinus.*—1.1 cm.
*Width of petiolar sinus.*—2.2 cm.
*Shape of upper sinuses.*—High widened, overlapped.
Color:
*Immature foliage upper side.*—Near RHS Yellow-Green 154D streaked 150D.
*Immature foliage under side.*—Near RHS Yellow-Green 154D streaked 150D.
*Mature foliage upper side.*—Near RHS Green 137A.
*Mature foliage under side.*—Near RHS Yellow-Green 144A.
Venation: Type: pinnate.
*Venation color upper side.*—Near RHS Yellow-Green 154C.
*Venation color under side.*—Near RHS Yellow-Green 154C.
Petiole:
*Length.*—15 cm.
*Diameter.*—0.6 cm.
*Color.*—Near RHS Yellow-Green 144A with weak Anthocyanin presence near base, Red 36C.
*Texture.*—Glabrous.

FLOWER

Flowering period begins around May 6 to 10 in Murcia, Spain.
Inflorescence when in bud:
*Length.*—13 cm.
*Diameter.*—5 cm.
*Bud color.*—Near RHS Green 140B.
*Bud shape.*—Conical.
*Bud size.*—About 1 to 2 mm by 1 to 2 mm.
Individual flower:
*Main time of flowering.*—5 days.
*Length of entire flower* (*to end of stamens*).—0.7 cm.
*Calyx shape.*—Funnel.
*Calyx width.*—1.5 cm.
*Calyx color.*—Near RHS Green 140B.
*Calyx apex.*—Rounded.
*Calyx base.*—Rounded.
*Calyx texture.*—Glabrous all surfaces.
*Diameter.*—15 mm.
*Quantity per flowering stem.*—5.
*Days lasting on plant.*—5 days.
Petals:
*Quantity* 5.
*Arrangement.*—Symmetrical rotate.
*Length.*—0.2 cm.
*Width.*—<0.1 cm.
*Shape.*—Obovate.
*Apex.*—Ovate.
*Base.*—Ovate.
*Texture, upper and lower surfaces soft.*
*Color.*—At opening upper surface: Near RHS Green 140B. At opening lower surface: Near RHS Green 140B. Fully opened upper Surface: Near RHS Green 140B. Fully opened lower Surface: Near RHS Green 140B.

Peduncles:
*Fruit peduncle length.*—55 mm.
*Fruit peduncle width.*—5 mm.
*Angle.*—About 70° to the lateral branch.
*Fruit peduncle strength.*—Firm-hard.
*Fruit peduncle texture.*—Soft.
*Color.*—Light green (142D RHS).
Pedicels:
*Length.*—0.7 cm.
*Diameter.*—0.2 cm.
*Angle.*—About 70° to center of flower cluster.
*Strength.*—Medium.
*Texture.*—Softly pubescent.
*Color.*—Near RHS Green 141C.
*Fragrance.*—Absent.

REPRODUCTIVE ORGANS

*Number of stamens.*—5.
*Anthers.*—Shape: oblong. Length: Approximately 0.1 cm. Color: Near Yellow 9C.
*Pollen.*—Color: Near Yellow 8A.
*Quantity.*—Abundant.
*Pistil quantity.*—1. Length; 0.3 cm.
*Style.*—Length: <0.1 cm. Color: Near RHS Green 143C.
*Stigma.*—Shape: round. Color: Near RHS Yellow-Green 144D.
*Ovary color.*—Near RHS Yellow-Green 144D.

FRUIT

Cluster:
*Average length.*—28 cm.
*Average diameter.*—19 cm.
*Average weigh.*—750 grams.
*Fertility index.*—Number of clusters per sprouted buds 1,3.
*Cluster density.*—Medium (densely distributed berries, pedicels not visible, berries movable).
Fruit:
*Average length.*—2.8 cm.
*Average diameter.*—2.3 cm.
*Shape.*—Obovoid.
*Cross-section.*—Circular.
*Color of berry skin.*—Near RHS Yellow-Green 150A.
*Color of berry flesh.*—Translucent, near White 155B.
*Brix at harvest.*—19.
*Ease of detachment from pedicle.*—Difficult, well hooked and difficult detachment.
*Thickness of skin.*—Thin.
*Firmness of flesh.*—Crunchy and very firm.
*Particular flavor.*—Neutral aromatic.
*Fruit peduncle length.*—55 mm.
*Fruit peduncle width.*—6 mm.
*Fruit peduncle texture.*—Firm, hard.
*Fruit peduncle color.*—Near Green 142D.
*Formation of seeds.*—Rudimentary.
*Date of berry ripening.*—Beginning in early July.

OTHER CHARACTERISTICS

Disease and pest resistance: Not observed to be susceptible nor resistant to normal diseases and pests of *Vitis vinifera*.

Temperature tolerance: Observed growing between 6° C. to 41° C.

Temperature tolerance: Observed to tolerate water shortages during the dry Summer months of Murcia, Spain without detriment.

What is claimed is:

1. A new and distinct cultivar of *Vitis* grapevine named 'Itumsixteen' as herein illustrated and described.

* * * * *